United States Patent
Griesgraber et al.

(10) Patent No.: US 10,246,472 B2
(45) Date of Patent: Apr. 2, 2019

(54) GUANIDINE-FUNCTIONALIZED PARTICLES AND METHODS OF MAKING AND USING

(71) Applicant: 3M INNOVATIVE PROPERTIES COMPANY, St. Paul, MN (US)

(72) Inventors: George W. Griesgraber, Eagan, MN (US); Robert T. Fitzsimons, Jr., Minneapolis, MN (US); Douglas A. Hanggi, Woodbury, MN (US); Masayuki Nakamura, Woodbury, MN (US); Jerald K. Rasmussen, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 232 days.

(21) Appl. No.: 15/488,716

(22) Filed: Apr. 17, 2017

(65) Prior Publication Data
US 2017/0217995 A1    Aug. 3, 2017

Related U.S. Application Data

(62) Division of application No. 14/437,769, filed as application No. PCT/US2013/070946 on Nov. 20, 2013, now Pat. No. 9,657,038.

(Continued)

(51) Int. Cl.
C07F 7/18         (2006.01)
B01D 15/00        (2006.01)
(Continued)

(52) U.S. Cl.
CPC ............ *C07F 7/1804* (2013.01); *B01D 15/00* (2013.01); *B01D 24/00* (2013.01); *B01J 20/103* (2013.01); *B01J 20/22* (2013.01); *B01J 20/28004* (2013.01); *B01J 20/286* (2013.01); *B01J 20/289* (2013.01); *B01J 20/28083* (2013.01); *B01J 20/28085* (2013.01); *B01J 20/3204* (2013.01); *B01J 20/3219* (2013.01); *B01J 20/3244* (2013.01); *B01J 20/3293* (2013.01); *C07F 7/1872* (2013.01); *C07F 7/1892* (2013.01); *C12M 25/16* (2013.01); *G01N 1/405* (2013.01); *B01J 2220/80* (2013.01)

(58) Field of Classification Search
None
See application file for complete search history.

(56) References Cited

U.S. PATENT DOCUMENTS 5,922,449 A    7/1999   Revis
5,925,552 A    7/1999   Keogh et al.
(Continued)

FOREIGN PATENT DOCUMENTS

CN    102533725 A    7/2012
JP    2007-314730    12/2007
(Continued)

OTHER PUBLICATIONS

Mdoe et al. Tanz. J. Sci. 2011, 37, 156-166 (Year: 2011).*
(Continued)

*Primary Examiner* — Clare M Perrin
(74) *Attorney, Agent, or Firm* — Kenneth B. Wood

(57) ABSTRACT

Guanidine-functionalized particles and methods of making and using such particles.

19 Claims, 1 Drawing Sheet

Related U.S. Application Data

(60) Provisional application No. 61/733,156, filed on Dec. 4, 2012.

(51) Int. Cl.

| | | |
|---|---|---|
| *C12M 1/12* | (2006.01) | |
| *B01J 20/286* | (2006.01) | |
| *B01D 24/00* | (2006.01) | |
| *G01N 1/40* | (2006.01) | |
| *B01J 20/10* | (2006.01) | |
| *B01J 20/22* | (2006.01) | |
| *B01J 20/28* | (2006.01) | |
| *B01J 20/289* | (2006.01) | |
| *B01J 20/32* | (2006.01) | |

(56) References Cited

U.S. PATENT DOCUMENTS

| | | | | |
|---|---|---|---|---|
| 6,057,377 | A * | 5/2000 | Sasaki | C03C 1/006 |
| | | | | 210/656 |
| 6,251,280 | B1 * | 6/2001 | Dai | B01J 20/28083 |
| | | | | 210/198.2 |
| 6,284,470 | B1 | 9/2001 | Bitner et al. | |
| 6,733,828 | B2 * | 5/2004 | Chao | B01J 29/0308 |
| | | | | 427/230 |
| 7,125,488 | B2 | 10/2006 | Li | |
| 7,959,992 | B2 * | 6/2011 | Chen | B41M 5/52 |
| | | | | 427/203 |
| 2002/0162798 | A1 | 11/2002 | Johnson et al. | |
| 2006/0105391 | A1 | 5/2006 | Engel et al. | |
| 2006/0216206 | A1 * | 9/2006 | Hudson | B01J 20/28042 |
| | | | | 422/534 |
| 2008/0287661 | A1 * | 11/2008 | Jones | B01L 3/0275 |
| | | | | 530/418 |
| 2009/0048439 | A1 | 2/2009 | Weisburg et al. | |
| 2009/0246885 | A1 | 10/2009 | Bian | |
| 2011/0217752 | A1 * | 9/2011 | Rasmussen | C08G 69/10 |
| | | | | 435/183 |
| 2012/0252008 | A1 | 10/2012 | Brown et al. | |
| 2014/0284278 | A1 | 9/2014 | Haymore | |

FOREIGN PATENT DOCUMENTS

| | | | | |
|---|---|---|---|---|
| WO | WO 2011/109151 | A1 | 9/2011 | |
| WO | WO-2011109151 | A1 * | 9/2011 | C08G 69/10 |
| WO | WO 2012-134636 | | 10/2012 | |

OTHER PUBLICATIONS

Kramer et al. (Separation and Purification Technology, 2006, 1, 81-185 (Year: 2006).*
Faria et al. Applied Catalysis A, 2008, 338, 72-78 (Year: 2008).*
Kim et al., "Preparation of guanidine bases immobilized on SBA-15 mesoporous material and their catalytic activity in knoevenagel condensation", Studies in Surface Science and Catalysis, vol. 146, Jan. 1, 2003, pp. 505-508.
Extended European Search Report, EP13860076.2, dated Jul. 4, 2016, 3 pages.
Balbino, "Silica-Supported Guanidine Catalyst for Continuous Flow Biodiesel Production", Green Chemistry, 2011, vol. 13, No. 11, pp. 3111-3116.
Bothof; "Salt tolerant ligands and polymers for membrane absorber applications", American Chemical Society National Meeting, Mar. 2011, p. 55.
Brunel, "Functionalized Micelle-Templated Silicas (Mts) and Their Use as Catalysts for Fine Chemicals", Microporous and Mesoporous Materials, 1999, vol. 27, pp. 329-344.
Candei, "Sensing properties of silica nanoparticles functionalized with anion binding sites and sulforhodamine B as fluorogenic signaling unit", Inorganica Chemica Acta, 2012, vol. 381, pp. 188-194.
Faria, "Tetramethylguanidine Covalently Bonded Onto Silica •Gel Surface as an Efficient and Reusable Catalyst for Transesterification of Vegetable Oil", Applied Catalysis A: General, 2008, vol. 338, pp. 72-78.
Ju, "Synthesis and Characterization of Ordered Mesoporous Anion-Exchange Inorganic/Organic Hybrid Resins for Radionuclide Separation", Ind. Eng. Chem. Res., 2000, vol. 39, pp. 550-553.
Khamlichi, "Specific Adsorption of Serine Proteases on Coated Silica Beads Substituted With Amidine Derivatives", Journal of Chromatography, 1990, vol. 510, pp. 123-132.
Kramer, "Guanidiniun Functionalised Silica-Based Anion Exchangers Significantly Improve the Selectivity of Platinum Group Metal Recovery From. Process Solutions", Separation and Purification Technology, 2006, vol. 49, pp. 181-185.
Mdoe, "Preparation of Tetramethylguanidine-functionalized mesoporous silica as a catalyst for the epoxidation of electron deficient alkenes", Tanzania Journal Science, 2011, vol. 37, pp. 156-166.
Riordan; Salt Tolerant Membrane Absorbers for Robust Impurity Clearance; Biotechnology, Sep. 2009, vol. 25, No. 2, pp. 1695-1702.
Sasaki, "Solid-State 31p NMR Study of Phosphonate Binding Sites in Guanidine-Functionalized, Molecular Imprinted Silica Xerogels", 2000, vol. 12, pp. 1400-1407.
Slowing, "Effect of Surface Functionalization of MCM-41-Type Mesoporous Silica Nanoparticles on the Endocytosos by Human Cancer Cells", J. Am. Chem. Soc., Nov. 2006, vol. 128, pp. 14792-14793.
International Search report for PCT International Application No. PCT/US2013/070946 dated Feb. 26, 2014, 3 pages.

* cited by examiner

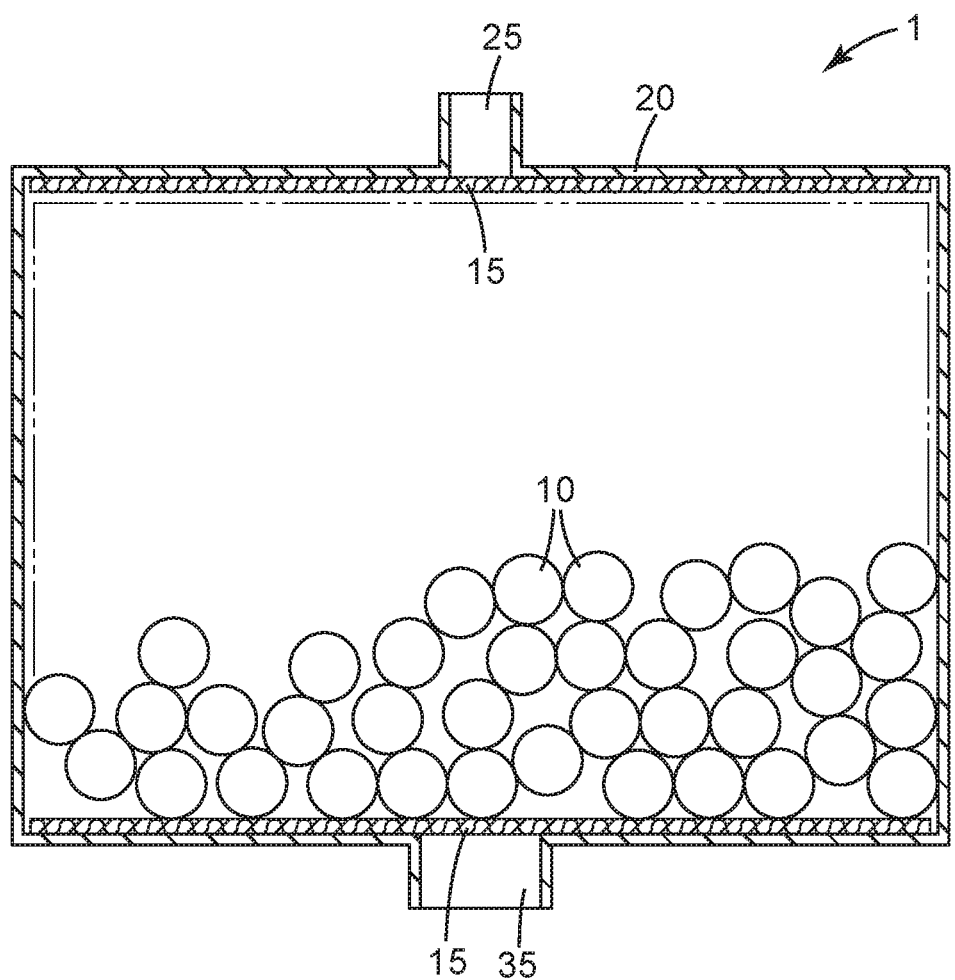

GUANIDINE-FUNCTIONALIZED PARTICLES AND METHODS OF MAKING AND USING

BACKGROUND

The capture of target biomaterials (such as, for example, constituents or products of living cells, e.g. proteins, viruses, and so on) for purposes such as purification, isolation, detection, and the like, has long been an objective of investigators.

SUMMARY

In broad summary, herein are disclosed guanidine-functionalized particles and methods of making and using such particles. These and other aspects of the invention will be apparent from the detailed description below. In no event, however, should the above summary be construed to limit the claimable subject matter, whether such subject matter is presented in claims in the application as initially filed or in claims that are amended or otherwise presented in prosecution.

BRIEF DESCRIPTION OF THE DRAWING

The FIGURE is a side schematic cross sectional view of an exemplary fluid-purification device comprising a container within which are entrapped guanidine-functionalized particles.

All FIGURES and formulas in this document are not to scale and are chosen for the purpose of illustrating different embodiments of the invention. In particular the dimensions of the various components and substituents are depicted in illustrative terms only, and no relationship between the dimensions of the various components and substituents should be inferred from the drawings, unless so indicated.

DETAILED DESCRIPTION

Disclosed herein are guanidine-functionalized particles and methods of making and using such particles. A guanidine-functionalized particle may be any particle comprising at least one ligand comprising a guanidine group, in which the ligand comprises the structure shown in Formula 1:

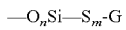     Formula 1

In Formula 1, —O is an oxygen atom that is covalently bonded to the particle, and n is 1, 2 or 3. Si is a silicon atom to which the n oxygen atoms are covalently bonded. S is a spacer group that is covalently bonded to the silicon atom, with m (designating the number of atoms in the backbone of the spacer group) being 2-16 inclusive of the endpoints and all integers in between. G denotes a guanidine group of the formula NH—C(NH)—NH$_2$.

A particle comprising a specific exemplary ligand within the general type represented by Formula 1 is shown in Formula 2:

Formula 2

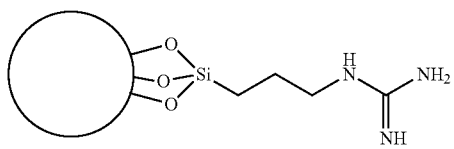

It will be understood that Formula 2 represents a specific embodiment in which n=3 and m=3 (with all three atoms of spacer group S being carbon). In Formulas 1 and 2, the ionization state of the guanidine group is omitted; it will be understood that in various environments such guanidine groups may be charged or uncharged (e.g., protonated or deprotonated) e.g. according to the pH of a liquid medium in which the guanidine group is present, as discussed later herein.

The covalent bond(s) between the oxygen(s) of the ligand and the particle can be conveniently obtained e.g. by reacting an Si-bonded hydrolyzable group of the ligand precursor with a hydroxyl group of the particle, as discussed in detail later herein. While the exemplary structure of Formula 2 shows three such bonded oxygens (i.e., n=3 in Formula 1), it will be appreciated that in various embodiments one, two or three such bonded oxygens can be provided. If less than three such oxygens are bonded to the silicon atom, other substituents (e.g., substituents that are not bonded to the particle, and which are not shown in Formula 1) may be present on the silicon. Similarly, while the exemplary structure of Formula 2 shows three atoms in the backbone of spacer group S, with the atoms all being carbon, in various embodiments any number of atoms from two to sixteen can be present. In some embodiments, at least one of the atoms of spacer group S may be a hetero atom (e.g., nitrogen or oxygen). In specific embodiments, spacer group S may comprise a secondary amine, as discussed later.

The particle may comprise any suitable particle to which the ligand can be attached. In some embodiments, the particle may be an insoluble particle (meaning it is not soluble in aqueous solution or organic solvent to any significant extent, i.e., not soluble at more than 0.1 g per 100 ml at 25° C.). In further embodiments, the particle may be an inorganic particle (rather than, e.g. a particle comprised of a largely organic polymeric network). In some embodiments, the particle may be a silica particle (e.g., comprised largely of SiO$_2$, and bearing sufficient surface hydroxyl groups to enable a desired number of ligands to be covalently attached thereto). In particular embodiments, the particle may be silica gel, which is defined herein as porous, vitreous silica that is synthetically made from sodium silicate and that has a primary particle size (diameter) of at least 10 microns. As such, silica gel particles are distinguished from materials such as fumed silica and precipitated silica (which, although they may sometimes form clumps in the size range of a few microns or more, have a much smaller primary particle size than that).

In various embodiments, the particle (e.g., silica gel) may comprise a particle size (i.e. diameter, or equivalent diameter, if non-spherical or irregular) of at least about 10, 15, 25, 35, or 75 microns. In further embodiments, the particle (e.g., silica gel) may comprise a particle size of at most about 1000, 500, 300, 150, 100, or 70 microns. In various embodiments, the particle (e.g., silica gel) may comprise a pore size (e.g., an average or nominal pore size as reported by the provider of the particle) of at least about 60, 120, 300, or 500 Angstroms. In further embodiments, the particle (e.g., silica gel) may comprise a pore size of at most about 3000, 2000, or 1000 Angstroms.

It will be appreciated that a guanidine group as described herein may be uncharged or charged (e.g., protonated) depending on the particular environment in which it is placed (e.g., depending on the pH of an aqueous buffer with which the guanidine-functionalized particle is brought into contact). In environments in which a guanidine group of a guanidine-functionalized particle is charged, the charged guanidine group may comprise an associated counterion. In some embodiments such a counterion may arise in the generation of the guanidine group (that is, the guanidine group as produced in the synthesis reaction may be charged, and may have a counterion associated therewith, as discussed later herein). In other embodiments a counterion may not arise in the generation of the guanidine group (e.g., the guanidine group may be produced in the synthesis reaction as a free base), but the guanidine-containing ligand (e.g., the functionalized particle) may be later placed into an environment (e.g., a liquid buffer) in which the guanidine group becomes charged and a corresponding counterion becomes associated therewith. In still other embodiments, a particular counterion may be associated with the guanidine group (e.g. as synthesized), but the counterion may then be exchanged for a different counterion. The charge state of a guanidine group and the presence and identity and charge state of a counterion thus possibly varying with environment, it is emphasized that all references to guanidine groups in the claims herein, are irrespective of the charge state of the guanidine group and are irrespective of the presence or identity of an associated counterion, unless such charge state and/or presence and/or identity of a counterion is explicitly specified in the claim.

Furthermore, the concept of a counterion that is associated with a guanidine group is used broadly herein, and it will be understood that such a counterion may not necessarily be constantly located in close proximity to the same guanidine group. Furthermore, the guanidine group and the associated counterion do not necessarily have to always be fully solvated (e.g., in aqueous solution). That is, they may be present as salts in a partially or substantially dried product (e.g., a solid or semi-solid product), which product may be placed into a liquid (e.g., an aqueous buffer) and solvated as desired. In particular embodiments, an associated counterion of the guanidine group does not comprise a halogen (e.g., the counterion is not a chloride ion). In specific embodiments, the associated counterion is a sulfate and/or bisulfate ion. In other specific embodiments, the associated counterion is a hydroxide ion (as may result, for example, from putting a guanidine group in the free-base form into an unbuffered aqueous solution).

In some embodiments, a guanidine-functionalized particle can be made by a simple and convenient method using O-methylisourea hemisulfate (which is a readily available starting material, CAS No. 52328-05-9). In a first step of the method, O-methylisourea may be reacted with a linker molecule of the general structure shown in Formula 3:

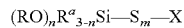    Formula 3

In Formula 3, RO is an alkoxy group that comprises one or two carbons, or is an acetoxy group (which alkoxy or acetoxy group is bonded to the silicon), and n is 1, 2 or 3. $R^a$ is an unreactive group (e.g., an alkyl group) that is bonded to the silicon (if such a group is present, noting that no such group will be present if n=3). S is a spacer group that is bonded to the silicon and that comprises a backbone with m atoms, and m is 2-16, inclusive. And, X is a primary amine that is capable of reacting with the O-methylisourea to form a guanidine group.

An exemplary first step of the method is shown in Formula 4:

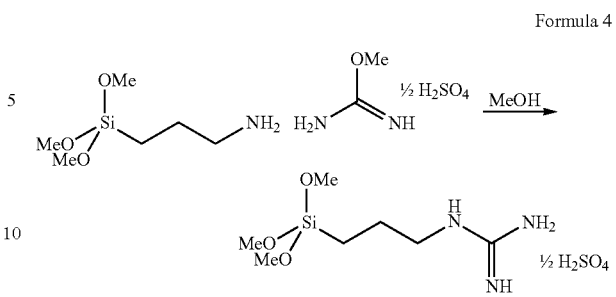

In this example, O-methylisourea is provided as a hemisulfate, and is reacted with 3-aminopropyltrimethoxysilane (in methanol) to form the guanidine group (noting that the charge state of the guanidine group and of the associated hemisulfate counterion are not shown in Formula 4).

In a second step of this method, at least one of the Si-bonded RO groups of the linker molecule (with Si atoms comprising one or more such reactive RO groups being well known by the term silane coupling agents) is reacted with a hydroxyl group of a suitable particle to form a covalent bond between the linker molecule and the particle. (It is emphasized that the terminology of "first" and "second" steps is used purely for convenience of description and that the steps can be performed in any desired order). For example, any or all of the three trimethoxy reactive groups of the linker molecule of Formula 4 may react with surface hydroxyl groups of the particle.

A net result of these two steps is summarized in exemplary embodiment in Formula 5:

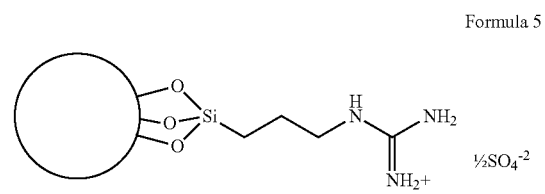

The specific exemplary representation of Formula 5 shows the thus-produced guanidine group in a positively charged (e.g., protonated) condition with a negatively charged hemisulfate counterion associated therewith. It will be understood that a guanidine-functionalized particle may be produced in such condition by the above method, but that the charge state of the guanidine group, the presence, identity and/or charge state of a counterion, etc., may be affected thereafter by the environment into which the guanidine-functionalized particle is placed, as discussed above.

It will be appreciated that Formulas 3-5 are representative examples and that any suitable linker molecule can be used (as long as the linker molecule includes e.g. a primary amine that can be reacted with the O-methylisourea to form a guanidine group), within the overall boundaries prescribed herein. For example, the linker molecule can comprise any desired number of any suitable reactive groups (e.g., ethoxy, methoxy, acetoxy) on the silicon atom (noting that if multiple reactive groups are present they do not have to be identical; further noting that if less than three such reactive groups are used, other (e.g., nonreactive) groups can be present, e.g. as shown in the general representation of Formula 3, and still further noting that if multiple nonreactive groups are present they do not have to be identical). In a specific example, 3-aminopropyltriethoxysilane may be used as the linker molecule rather than the 3-aminopropyltrimethoxysilane shown in Formula 4.

Furthermore, although Formula 4 depicts a spacer group S with a backbone of three atoms and with all of these atoms being carbon, any number of atoms from two to sixteen may be used. And, in some embodiments, at least one of the atoms, e.g. backbone atoms, of spacer group S may be a hetero atom (e.g., nitrogen or oxygen). In some specific embodiments, the spacer group of the linker molecule may comprise a secondary amine. In a particular example of this type, the linker molecule may be e.g. N-(2-aminoethyl)-3-aminopropyltrimethoxysilane (available under the trade designation SIA0591.0 from Gelest, Inc., Tullytown, Pa.), as demonstrated in the Working Examples herein. Other potentially useful linker molecules may include e.g. (aminoethylaminomethyl) phenethyltrimethoxysilane (SIA0588.0, Gelest), N-(2-aminoethyl)-3-aminopropylmethyldimethoxysilane (SIA0589.0, Gelest), N-(6-aminohexyl) aminopropyltrimethoxysilane (SIA0594.0, Gelest), N-(2-aminoethyl)-11-aminoundecyltrimethoxysilane (SIA0595.0, Gelest), N-3 [(amino(polypropylenoxy)] aminopropyltrimethoxysilane (SIA0599.4, Gelest), 3-aminopropyldimethylethoxysilane (SIA0603.0, Gelest), 3-aminopropylmethyldiethoxysilane (SIA0605.0, Gelest), aminopropylsilanetriol (SIA0608.0, Gelest), 3-aminopropyltriethoxysilane (SIA0610.0, Gelest), 3-aminopropyltrimethoxysilane (SIA0611.0, Gelest), and (3-trimethoxysilylpropyl)diethylenetriamine (SIT8398.0, Gelest). Mixtures of any of the herein-mentioned linker molecules may be used if desired.

The particle may comprise any suitable particle comprising a hydroxyl group with which a reactive moiety (e.g., a silicon-bonded methoxy, ethoxy, or acetoxy group of a silane-coupling-agent moiety) of the linker molecule can react. In some embodiments, the particle may be an insoluble particle, an inorganic particle, a silica particle, or a silica gel particle, all as defined and described earlier herein. In various embodiments, the particle (e.g., silica gel) may comprise a particle size (diameter, or equivalent diameter, if non-spherical or irregular) of at least about 10, 15, 25, 35, or 75 microns. In further embodiments, the particle (e.g., silica gel) may comprise a particle size of at most about 1000, 500, 300, 150, or 100 microns. In various embodiments, the particle (e.g., silica gel) may comprise a pore size (e.g., an average or nominal pore size as reported by the provider of the particle) of at least about 60, 120, 300, or 500 Angstroms. In further embodiments, the particle (e.g., silica gel) may comprise a pore size of at most about 3000, 2000, or 1000 Angstroms.

The general methods-of-making described above, and materials used therein, may be tailored as desired for particular purposes. Thus, in some embodiments, each thus-formed ligand on the particle may only have a single guanidine group (rather than there being e.g. two, three or more guanidine groups on a given ligand). In some embodiments, the thus-formed guanidine-comprising ligands may be the only ligands on the particle (rather than there being additional ligands, e.g. silane-coupled ligands, on the particle, which additional ligands do not comprise a guanidine group). In some embodiments, a substantial amount (e.g., an amount readily detectable by surface analysis) of residual hydroxyls are present on the surface of the particle even after the attachment of the linker molecules to some of the hydroxyls of the particle to form ligands thereon (e.g., rather than the residual hydroxyls being endcapped). In some embodiments, the methods disclosed herein do not include a step of equilibrating the particle in an atmosphere having a defined relatively humidity (e.g., of less than 40%) prior to the reacting of the linker molecule with a surface hydroxyl group of the particle. In some embodiments, the step of reacting a reactive group of a silane-coupling-agent moiety of the linker molecule with a surface hydroxyl group of the particle is carried out in a liquid mixture, which liquid mixture does not contain any imprinting molecule(s) of the type that are used in the well-known process of molecular imprinting. It is also noted that in some cases particles (e.g., silica gel particles) might be obtained with any of the above-mentioned linker molecules already reacted with hydroxyl groups of the particle so that the linker molecules are already bonded to the particle. Thus in particular embodiments, the step of reacting at least one of the RO groups of a linker molecule with a hydroxyl group of a particle to form a covalent bond between the linker molecule and the particle (e.g., as it appears in method claims herein) is defined herein as encompassing the special case in which particles are obtained with linker molecules having already been bonded thereto (e.g. by another party).

While the method outlined in Formulas 3-5 uses O-methylisourea, it will be appreciated that other starting materials might be used to make a guanidine-containing linker of the general structure of Formula 1. Such starting materials might include e.g. O-alkylisourea salts such as O-methylisourea sulfate, O-methylisourea hydrogen sulfate, O-methylisourea acetate, O-ethylisourea hydrogen sulfate, and O-ethylisourea hydrochloride. Beyond these materials, other starting materials that might be used to make a guanidine-containing linker of the general structure of Formula 1 might include e.g. cyanamide, chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride. It will be appreciated that some of these starting materials may produce a guanidine-containing linker in which the guanidine group is in a specific charge state (e.g., is a free base or is positively charged) and/or has a specific counterion associated therewith. It will be understood that such a guanidine group may be placed into a specific charge state, may have its associated counterion exchanged for some other counterion, and so on, based on the disclosures herein.

Also disclosed herein are methods of using guanidine-functionalized particles to capture one or more target biological species that may be present in a fluid (e.g., a liquid solution, mixture, suspension, etc.). Such methods may include the steps of contacting a fluid (that potentially contains one or more target biological species) with a guanidine-functionalized particle; allowing a target biological species in the fluid to non-specifically bind with a guanidine group of the guanidine-functionalized particle; and, separating the fluid and the guanidine-functionalized particle with the target biological species non-specifically bound thereto, from each other. By non-specific binding is meant that the interaction and association between the guanidine group and the target biological species is due to one or more of ionic interaction, hydrogen-bonding, and/or hydrophobic interaction, rather than by some specific recognition of a target molecule or portion thereof based on the particular size, shape, and/or any other property, of the molecule or portion thereof. As such, the term non-specific binding as used herein, by definition does not encompass such bonding as occurs in the method commonly referred to as molecular imprinting (e.g., as described in U.S. Pat. No.

6,057,377), nor does it encompass any method based on antigen-antibody or enzyme-substrate (e.g., lock-and-key or affinity-type) binding.

It will be appreciated that the herein-disclosed non-specific binding will result in a target biological species being captured by the particle to a sufficient extent that the species remains with the particle upon the fluid and the particle being separated from each other. Such capture can be contrasted e.g. to chromatographic processes in which the passage of a target species past a particle or collection of particles is merely slowed down somewhat e.g. so that the target species is eluted from the collection of particles somewhat more slowly than some other species is eluted.

In some embodiments, non-specific binding as disclosed herein may take the form of the exchange of a (negatively-charged) counterion that is initially associated with the guanidine group, with one or more negatively charged groups of a target biological species (thus causing the target biological species to be associated with, e.g. to remain generally in proximity to, the guanidine group). In some embodiments, non-specific binding as disclosed herein may take the form of hydrogen bonding (e.g., between one or more hydrogens of the guanidine group and one or more hydrogen-bond-receptive portions of a target biological species). It will be appreciated that in various circumstances any or all of these interactions may contribute to the non-specific binding of a target biological species.

A target biological species can be any material or materials that are desired to be captured (so as to be e.g. removed from a fluid). As such, a target biological species may be a contaminant that is desired to be removed from some other component or material in the fluid, or may be a species of interest that is desired to be used (e.g., analyzed, manipulated, reacted, etc.) after being removed from the fluid. In some embodiments, such target biological species may comprise one or more biomacromolecules and/or microbiological species. Such biomacromolecules may include e.g. proteins, enzymes, nucleic acids, and fragments derived from any of these. Specific examples of biomacromolecules that might be desired to be removed from a fluid include e.g. host cell proteins or host cell DNA from cell cultures used for the preparation of therapeutic antibodies. Such microbiological species may include e.g. bacteria, viruses, cells, spores, and fragments or debris derived from any of these. These examples are non-limiting and it will be understood that the terms biomacromolecule and microbiological species are used very broadly herein, and it will also be understood that there may be no firm dividing between the two. It will further be appreciated that in many uses, a fluid might contain a mixture of many different target species, a portion of any or all of which may be desired to be captured. Thus, the methods disclosed are not limited to the capture of a single target species from a fluid.

As mentioned, in some embodiments a target biological species may comprise one or more impurities, contaminants, byproducts, etc., which it is desired to remove from a fluid. As such, the guanidine-functionalized particles may be provided in a form which facilitates such a method. In the exemplary embodiment of the FIGURE, fluid-purification device 1 is shown which comprises a plurality of guanidine-functionalized particles 10, which particles 10 are entrapped (e.g., as a particle bed) within a container 20 (e.g., by way of mesh 15 that permits passage of fluids and sufficiently small particles therethrough, but does not permit guanidine-functionalized particles 10 to pass). A fluid that is desired to be purified can be injected into the container (e.g., through inlet 25) and can pass through a bed of particles 20 and can then exit the container (e.g., through outlet 35). At least some of a target biological species may be captured by the particles and thus remain within container 20 even as the fluid exits the container. The fluid can be actively pumped through the container, can flow through as motivated by gravity, etc. The fluid can contact the particle bed without stopping; or, it can be held in e.g. quiescent contact with the particle bed for a desired period.

It will be appreciated that the FIGURE merely provides an exemplary illustration (e.g., of a cartridge filter type apparatus) and that the methods disclosed herein can be carried out by way of any suitable apparatus. As such, the term container is used broadly to denote any receptacle in which the particles can be presented so as to be contactable with a desired fluid; the container does not have to be completely or even nearly-completely enclosed. Similarly the concept of the particles being entrapped within a container is used broadly herein. For example, both of these concepts encompass cases in which guanidine-functionalized particles are contacted with a desired fluid and placed onto or into a filtration apparatus (e.g., a Buchner funnel) that removes the fluid while leaving the guanidine-functionalized particles (and target species captured thereby) entrapped thereon (e.g., held atop a piece of filter paper used with the filtration apparatus). In another specific example, the guanidine-functionalized particles may be e.g. slurry-packed or flow-packed into a container (e.g., a column), then contacted with the desired fluid (whether on a continuous-flow or static basis) to capture at least some of the target biological species. The purified fluid may then be e.g. removed from the container. In another specific example, the desired fluid may be mixed with the guanidine-functionalized particles (e.g., under agitation) in a suitable container for a specified time, agitation may then be stopped to allow the particles with captured target biological species to settle to toward the bottom of the container, and the purified supernatant fluid may be removed from near the top of the container. It will be appreciated in general that the concept of separating (from each other) a fluid and a collection of guanidine-functionalized particles with a target biological species non-specifically bound thereto, includes cases in which at least some of the purified fluid is removed from the collection of particles, and also cases in which at least some of the particles of the collection of particles are removed from the purified fluid.

It will also be appreciated that the conditions under which the guanidine-functionalized particles are contacted with the fluid (e.g., the size of the particles and the density and manner in which they are provided in a receptacle, the flow rate of the fluid, the temperature of the fluid, and so on) can be chosen to enhance the capture of one of more target biological species. In particular, the pH of the liquid, and the presence of various ionic buffers in the fluid, may be manipulated e.g. to facilitate exchange of counterions associated with the guanidine groups, with negatively-charged groups of target biological species.

It has been found that the herein-disclosed guanidine-functionalized particles may be particularly effective in capturing target biological species even in the presence of high ionic strength conditions, i.e. high salt (e.g., NaCl) concentrations, that is, of 50, 100, 150, 200, or even 300 millimolar or more. It will be appreciated that this is highly advantageous since many industrially-important purification processes occur at relatively high ionic strength conditions. The ability of the herein-disclosed guanidine-functionalized particles to function well in such high ionic strength conditions/high salt concentrations is evidenced in the Working Examples herein. Specifically, tolerance for high-salt conditions (as evidenced by their ability to capture Bovine Serum Albumin in such conditions) is demonstrated in comparison to a representative primary amine-functionalized ligand and to a representative quaternary ammonium-functionalized ligand. Surprisingly, the disclosed guanidine-functionalized particles were found to tolerate much higher salt levels than the representative quaternary ammonium-functionalized ligand and the representative primary amine-functionalized ligand, as presented in the Working Examples herein (see Table 2). This is surprising in view of the fact that the ordinary artisan would expect the interaction between any of these functional groups (guanidine, quat, and primary amine) and a biological species such as Bovine Serum Albumin to be a primarily electrostatic interaction which would be generally similarly degraded by the presence of a high salt concentration.

It has also been found that the pore size of the particles (e.g., silica particles, particularly silica gel particles) can be chosen to enhance the capture of target biological species. For instance, as demonstrated in the Working Examples herein, when the target biological species is of a molecular weight similar to that of Bovine Serum Albumin (a well-known protein of molecular weight in the range of 66 Da), a pore size in the range of e.g. 500-1000 may be optimum (see e.g. Table 1). Larger or smaller pore sizes may be chosen for target biological species of higher or lower molecular weight. Thus in various embodiments, the particles (e.g., silica gel) may comprise an average pore size of at least about 60, 120, 300, or 500 Angstroms. In further embodiments, the particles (e.g., silica gel) may comprise an average pore size of at most about 3000, 2000, or 1000 Angstroms. Similarly, the particle size of the guanidine-functionalized particles may be chosen e.g. to facilitate adequate flow rate of the fluid through the particle bed, and/or to enhance the ability of the particles and the fluid to be separated from each other. In various embodiments, the particles (e.g., silica gel) may comprise an average particle size of at least about 10, 15, 25, 35, or 75 microns. In further embodiments, the particles (e.g., silica gel) may comprise an average particle size of at most about 1000, 500, 300, 150, or 100 microns.

This application is a divisional application of U.S. patent application Ser. No. 14/437,769, now allowed, which was a national stage filing under 35 U.S.C. 371 of PCT/US2013/070946, filed 20 Nov. 2013, which claimed priority to U.S. Provisional Application No. 61/733,156, filed 4 Dec. 2012, the disclosures of each of which are incorporated by reference in their entirety herein.

LIST OF EXEMPLARY EMBODIMENTS

Embodiment 1

A method of making a guanidine-functionalized particle, comprising: reacting O-methylisourea hemisulfate with a linker molecule comprising the formula $(RO)_n R^a{}_{3-n} Si-S_m-X$; where RO is an alkoxy group comprising one or two carbons, or is an acetoxy group; where n is 1, 2 or 3; where $R^a$ is an unreactive group; where S is a spacer group comprising a backbone with m atoms; m is from 2-16, inclusive; and where X is a primary amine that is capable of reacting with the O-methylisourea to form a guanidine group; and, reacting at least one of the RO groups of the linker molecule with a hydroxyl group of the particle to form a covalent bond between the linker molecule and the particle.

Embodiment 2

The method of embodiment 1 wherein the $(RO)_n Si$ moiety comprises a trimethoxysilane moiety.

Embodiment 3

The method of embodiment 1 wherein the linker molecule is 3-aminopropyltrimethoxysilane.

Embodiment 4

The method of embodiment 1 wherein the $(RO)_n Si$ moiety comprises a triethoxysilane moiety.

Embodiment 5

The method of any of embodiments 1-4 wherein all m atoms of the backbone of the spacer group S are carbon atoms.

Embodiment 6

The method of any of embodiments 1-5 wherein m=3.

Embodiment 7

The method of any of embodiments 1-4 and 6 wherein the spacer group S comprises at least one hetero atom.

Embodiment 8

The method of any of embodiments 1-4 and 6-7 wherein the spacer group S comprises at least one secondary amine.

Embodiment 9

The method of embodiment 8 wherein the linker molecule is N-(2-aminoethyl)-3-aminopropyltrimethoxysilane.

Embodiment 10

The method of any of embodiments 1-9 wherein the particle comprises a silica particle.

Embodiment 11

The method of embodiment 10 wherein the particle comprises silica gel.

Embodiment 12

The method of embodiment 11 wherein the silica gel particle comprises a particle size of about 25-100 microns and a pore size of about 60-2000 Angstroms.

Embodiment 13

The method of embodiment 11 wherein the silica gel particle comprises a particle size of about 30-70 microns and a pore size of about 300-1000 Angstroms.

Embodiment 14

The method of any of embodiments 1-13 wherein the step of reacting at least one of the RO groups of the linker molecule with a hydroxyl group of the particle to form a covalent bond between the linker molecule and the particle, is performed after the reacting of the O-methylisourea hemisulfate with the linker molecule.

Embodiment 15

The method of any of embodiments 1-13 wherein the step of reacting at least one of the RO groups of the linker molecule with a hydroxyl group of the particle to form a covalent bond between the linker molecule and the particle, is performed before the reacting of the O-methylisourea hemisulfate with the linker molecule.

Embodiment 16

A guanidine-functionalized silica gel particle, comprising: a silica gel particle comprising at least one ligand comprising a guanidine group, the ligand comprising the formula $-O_nSi-S_m-G$, where $-O$ is an oxygen atom that is covalently bonded to the surface of the silica gel particle; n is 1, 2 or 3; S is a spacer group comprising a backbone with m atoms; m is 2-16, inclusive; G is a guanidine group of the formula $NH-C(NH)-NH_2$; and wherein the guanidine group is charged and comprises an associated counterion and wherein the counterion does not comprise a halogen.

Embodiment 17

The particle of embodiment 16 wherein all m atoms of the backbone of the spacer group S are carbon atoms.

Embodiment 18

The particle of any of embodiments 16-17 wherein m=3.

Embodiment 19

The particle of any of embodiments 16 and 18 wherein the spacer group S comprises a secondary amine.

Embodiment 20

The particle of any of embodiments 16-19 wherein the guanidine group is the reaction product of a primary amine and O-methylisourea hemisulfate.

Embodiment 21

The particle of any of embodiments 16-20 wherein the silica gel particle comprises a particle size of about 25-100 microns and a pore size of about 60-2000 Angstroms.

Embodiment 22

The particle of any of embodiments 16-20 wherein the silica gel particle comprises a particle size of about 35-70 microns and a pore size of about 300-1000 Angstroms.

Embodiment 23

The particle of any of embodiments 16-22 wherein the ligand is the reaction product of one or more hydroxyl groups of the silica particle with one or more reactive groups of a silane coupling agent moiety of the ligand.

Embodiment 24

A fluid-purification device comprising a plurality of the particles of any of embodiments 16-23, entrapped within a container that is configured to accept a fluid to be purified and to allow the purified fluid to be removed therefrom.

Embodiment 25

A fluid purification device comprising a plurality of particles made by the method of any of embodiments 1-15, which particles are entrapped within a container that is configured to accept a fluid to be purified and to allow the purified fluid to be removed therefrom.

Embodiment 26

The fluid-purification device of any of embodiments 24-25 wherein the fluid-purification device is configured so that upon removal of the purified fluid from the container, a target biological species that is captured from the fluid by the guanidine-functionalized particles, remains within the container with the entrapped particles.

Embodiment 27

A method of separating a target biological species from a fluid, comprising: contacting the fluid with a guanidine-functionalized particle; allowing the target biological species to non-specifically bind with a guanidine group of the guanidine-functionalized particle wherein the guanidine group is of the formula $NH-C(NH)-NH_2$; and, separating the fluid and the guanidine-functionalized particle with the target biological species non-specifically bound thereto, from each other.

Embodiment 28

The method of embodiment 27 wherein the guanidine group is provided by the reaction product of a primary amine with O-methylisourea hemisulfate.

Embodiment 29

The method of any of embodiments 27-28 wherein the guanidine group is present on a ligand that is attached to the particle by way of one or more Si—O bonds.

Embodiment 30

The method of any of embodiments 27-29 wherein the ligand comprises a spacer group that comprises a backbone with from 2-16 atoms, inclusive.

Embodiment 31

The method of any of embodiments 27-30 wherein the particle is a silica gel particle.

Embodiment 32

The method of any of embodiments 27-31 wherein the particle comprises a particle size of about 25-100 microns and a pore size of about 60-2000 Angstroms.

Embodiment 33

The method of any of embodiments 27-32 wherein the fluid has an NaCl content of from about 50 millimolar to about 300 millimolar.

Embodiment 34

The method of any of embodiments 27-32 wherein the fluid has an NaCl content of from about 150 millimolar to about 300 millimolar.

Embodiment 35

The method of any of embodiments 27-34 wherein the target biological species comprises at least one negatively-charged moiety and wherein the guanidine group comprises a negatively-charged counterion associated therewith, and wherein the non-specific binding of the target biological species with the guanidine group comprises exchanging the negatively-charged counterion with the negatively-charged moiety of the target biological species.

Embodiment 36

The method of embodiment 35 wherein the negatively-charged counterion does not comprise a halogen atom.

Embodiment 37

The method of embodiment 36 wherein the negatively-charged counterion comprises a sulfate, bisulfate, or hydroxide anion.

Embodiment 38

The method of any of embodiments 27-37 wherein the target biological species comprises one or more biomacromolecules chosen from the group including proteins, enzymes, nucleic acids, and fragments derived from any of these; and/or, wherein the target biological species comprises one or more microbiological species chosen from the group including bacteria, viruses, cells, spores, and fragments or debris derived from any of these.

Embodiment 39

The method of any of embodiments 27-38 wherein the target biological species comprises one or more impurities in the fluid and wherein after the separating of the fluid and the particle with the target biological species non-specifically bound thereto from each other, the fluid comprises a purified solution or mixture containing at least one desired biological species.

Embodiment 40

The method of any of embodiments 27-39 wherein a plurality of the guanidine-functionalized particles are provided in a container that is configured to accept the fluid to be purified and wherein the method includes the step of removing the purified fluid from the container while retaining the guanidine-functionalized particles in the container with at least some target species having been captured by the guanidine-functionalized particles and remaining in the container therewith when the purified fluid is removed.

Embodiment 41

A method of separating a target biological species from a fluid, comprising: contacting the fluid with a guanidine-functionalized particle of the composition of any of embodiments 16-26; allowing the target biological species to non-specifically bind with a guanidine group of the guanidine-functionalized particle wherein the guanidine group is of the formula NH—C(NH)—NH$_2$; and, separating the fluid and the guanidine-functionalized particle with the target biological species non-specifically bound thereto, from each other.

Embodiment 42

A method of separating a target biological species from a fluid, comprising: contacting the fluid with a guanidine-functionalized particle made by the method of any of embodiments 1-15; allowing the target biological species to non-specifically bind with a guanidine group of the guanidine-functionalized particle wherein the guanidine group is of the formula NH—C(NH)—NH$_2$; and, separating the fluid and the guanidine-functionalized particle with the target biological species non-specifically bound thereto, from each other.

EXAMPLES

Reagents and Materials (3-Aminopropyl)trimethoxysilane (Catalog number A11284), O-methylisourea hemisulfate (Catalog number B22036) and N-(2-Aminoethyl)-3-aminopropyltrimethoxysilane (Catalog number A16981) were obtained from Alfa Aesar. N-Trimethoxysilylpropyl-N,N,N-trimethylammonium chloride was obtained from Gelest, Inc. (Catalog number SIT8415.0) as a 50% solution in methanol. Anhydrous methanol was obtained from J. T. Baker. Bovine Serum Albumin (BSA, Fraction V) was obtained from EMD Chemicals Inc.

Various silica gels were obtained as follows: DAISOGEL SP-1000-10 (approximately 11 micron diameter particles with approximately 1000 Angstrom pores) and DAISOGEL SP-300-10 (approximately 10 micron diameter particles with approximately 300 Angstrom pores) were obtained from Daiso Co. Ltd., Osaka Japan. DAVISIL 634 (approximately 75-150 micron diameter particles with approximately 60 Angstrom pores) was obtained from Aldrich Chemical Co. DAVISIL XWP500A (approximately 35-70 micron diameter particles with approximately 500 Angstrom pores), DAVISIL XWP1000A (approximately 35-70 micron diameter particles with approximately 1000 Angstrom pores) and DAVISIL XWP1000A (approximately 16-24 micron diameter particles with approximately 1000 Angstrom pores) were obtained from Grace Davison Discovery Science. And, GEDURAN 60 (approximately 40-63 micron diameter particles with approximately 60 Angstrom pores) was obtained from EMD Chemicals Inc. (All particle size and pore size ranges are as reported by the supplier).

3-Guanidinopropyltrimethoxysilane hemisulfate

A suspension of O-methylisourea hemisulfate (50.0 g, 0.407 mol) in anhydrous methanol (400 mL) was treated with 3-aminopropyltrimethoxysilane (70.9 mL, 0.407 mol). The reaction mixture was stirred under an atmosphere of nitrogen for 3 days. The reaction mixture was then concentrated under reduced pressure to give 116.8 g of the title compound as a waxy solid. $^1$H NMR analysis (CD$_3$OD, 500 MHz) revealed the following parameters: δ 3.44 (s, 9H), 3.01 (m, 2H), 1.54 (m, 2H), 0.56 (m, 2H).

Working Example 1 (W1)

3-Guanidinopropyltrimethoxysilane hemisulfate (1.00 g) was placed in a 4 dram screw cap vial and dissolved in 10 mL of anhydrous methanol. DIASOGEL SP-1000-10 (5.00 g) was added to the reaction mixture and the vial was capped and held at 50° C. for approximately three days to facilitate reaction between the trimethoxysilane and the particles. The resulting guanidine-functionalized silica gel (e.g., of the general type represented by Formulas 2 and 5 herein) was isolated by filtration, rinsed with methanol and allowed to air dry. (All other functionalized silica gels disclosed in these Examples were produced in a generally similar manner, unless otherwise noted).

Working Example 2

Working Example 2 was prepared in similar manner to Working Example 1 except using DIASOGEL SP-300-10 as the silica gel.

Working Example 3

3-Guanidinopropyltrimethoxysilane hemisulfate (500 mg) was placed in a 4 dram screw cap vial and dissolved in 10 mL of anhydrous methanol. 2.5 g of DAVISIL XWP500A (35-70 micron particle size) was added to the reaction and the vial was capped and held at 50° C. for approximately three days. The resulting guanidine-functionalized silica gel was isolated by filtration, rinsed with methanol and allowed to air dry.

Working Example 4

Working Example 4 was prepared in similar manner to Working Example 3 using DAVISIL XWP1000A (35-70 micron particle size) as the silica gel.

Working Example 5

Working Example 5 was prepared in similar manner to Working Example 3 using DAVISIL XWP1000A (16-24 micron particle size) as the silica gel.

Working Example 6

Working Example 6 was prepared in similar manner to Working Example 3 using DAVISIL grade 634 as the silica gel.

Working Example 7

Working Example 7 was prepared in similar manner to Working Example 3 using GEDURAN Silica Gel 60 as the silica gel.

Working Example 8

A suspension of O-methylisourea hemisulfate (6.42 g, 52 mmol) in anhydrous methanol (50 mL) was treated with N-(2-aminoethyl)-3-aminopropyltrimethoxysilane (10.0 g, 45 mmol). The reaction mixture was stirred under an atmosphere of nitrogen for 3 days. The reaction mixture was then concentrated under reduced pressure to a waxy solid. A 0.6 g sample of this material was placed in a 4 dram screw cap vial and dissolved in 10 mL of anhydrous methanol. 2.5 g of DAVISIL XWP500A (35-70 micron) was added to the reaction and the vial was capped and held at 50° C. for approximately three days. The resulting guanidine-functionalized silica gel was isolated by filtration, rinsed with methanol and allowed to air dry.

Comparative Examples with Unfunctionalized Silica Gels

Comparative Example 1 (C1) was the DIASOGEL SP-1000-10 silica gel of Working Example 1, unfunctionalized (that is, used as-received rather than being functionalized with guanidine groups).

Comparative Example 3 (C3) was the DAVISIL XWP500A (35-70 micron particle size) silica gel of Working Example 3, unfunctionalized.

Static BSA Binding Capacity Test for Functionalized and Unfunctionalized Particles Static BSA (Bovine Serum Albumin) Binding Capacity measurements were carried out in the following general manner. Quantities (typically in the range of 10 mg-200 mg) of the silica particles were accurately weighed into 15-mL culture tubes and treated with an accurately measured amount (5.00 or 10.00 mL) of a solution of Bovine Serum Albumin (BSA, 2.1 mg/mL) in 10 mM 3-(N-morpholino) propanesulfonic acid (MOPS) buffer at pH 7.5. The samples were mixed by vortex for approximately 10 seconds and then rocked gently for about 24 hr. The samples were then centrifuged (nominal 3300 rpm) for about 15 minutes (the total time of BSA exposure was thus just over 24 hours, with exceptions as noted below). The supernatant was then passed through a 0.2 micron filter and absorbance was measured at approximately 279 nm. From the resulting graph, the x-intercept was taken as the amount of silica needed to capture all of the protein and this was used to calculate the maximum static binding capacity (SBC). The static binding capacity is reported on weight/weight basis (as mg of BSA per g of functionalized particle). The results of the Static Binding Capacity tests are presented in Table 1 (as Working Examples W1 through W7), with results for certain corresponding unfunctionalized particles (Comparative Examples C1 and C3) presented (in parentheses) alongside.

TABLE 1

| Example | Silica Gel Pore Size, Angstroms | Silica Gel Particle Size, Microns | Static Binding Capacity, mg/g |
| --- | --- | --- | --- |
| W1 (C1) | 1000 | 11 | 81[1]/78 (9) |
| W2 | 300 | 10 | 79[1]/154 |
| W3 (C3) | 500 | 35-70 | 217 (21) |
| W4 | 1000 | 35-70 | 136 |
| W5 | 1000 | 16-24 | 147 |
| W6 | 60 | 75-150 | 32 |
| W7 | 60 | 63-212 | 12 |
| W8 (C3) | 500 | 35-70 | 173 (21)[2] |

[1]30 minutes BSA exposure
[2]same unfunctionalized silica particles as in Comparative Example C3

Salt Tolerance

Comparative Examples with Functional Groups Other than Guanidine

Comparative Example C1-A 3-aminopropyltrimethoxysilane (500 mg) was placed in a 4 dram screw cap vial and dissolved in 10 mL of anhydrous methanol. DIASOGEL SP-1000-10 (2.5 g) was added to the reaction mixture and the vial was capped and held at 50° C. for approximately three days. The resulting primary-amine-functionalized silica gel was isolated by filtration, rinsed with methanol and allowed to air dry.

Comparative Example C1-B 3-trimethylammoniumpropyltrimethoxysilane (1.00 g, 50% solution in MeOH) was placed in a 4 dram screw cap vial and dissolved in 10 mL of anhydrous methanol. DIASOGEL SP-1000-10 (2.5 g) was added to the reaction mixture and the vial was capped and held at 50° C. for approximately three days. The resulting quaternary-ammonium-salt-functionalized silica gel was isolated by filtration, rinsed with methanol and allowed to air dry.

Comparative Example C3-A

Comparative Example C3-A was prepared in similar manner to Comparative Example C1-A except using DAVISIL XWP500A (35-70 micron particle size) as the silica gel, to provide a primary-amine-functionalized silica gel.

Comparative Example C3-B

Comparative Example C3-B was prepared in similar manner to Comparative Example C1-B except using DAVISIL XWP500A (35-70 micron particle size) as the silica gel, to provide a quaternary-ammonium-salt-functionalized silica gel.

Static BSA Binding Capacity Test for Functionalized Particles at High Salt Concentrations The particles of Working Examples 1 and of Comparative Examples C1-A and C1-B (all of which used DIASOGEL SP-1000-10 silica gel particles) were then tested for BSA Static Binding Capacity in the presence of various levels of NaCl. Similarly, the particles of Working Example 3 and Comparative Examples C3-A and C3-B (all of which used DAVISIL XWP500A silica gel particles) were tested for BSA Static Binding Capacity in the presence of various levels of NaCl. All of the testing was done in similar manner to that described above. The resulting Static Binding Capacities are shown in Table 2 (in mg/g, as above), as a function of the sample identity and the NaCl concentration (in millimolar (mM)).

TABLE 2

| Example | Silica Gel | Functional Group | NaCl concentration | | | |
| --- | --- | --- | --- | --- | --- | --- |
| | | | 0 mM | 50 mM | 150 mM | 300 mM |
| W1 | SP-1000-10 | Guanidine | 83 mg/g | 79 mg/g | 70 mg/g | 57 mg/g |
| C1-A | SP-1000-10 | Primary amine | 56 mg/g | 61 mg/g | 45 mg/g | 36 mg/g |
| C1-B | SP-1000-10 | Quaternary amine | 43 mg/g | 36 mg/g | 24 mg/g | 14 mg/g |
| W3 | XWP500A | Guanidine | 202 mg/g | ND | ND | 160 mg/g |
| C3-A | XWP500A | Primary amine | 176 mg/g | ND | ND | 115 mg/g |
| C3-B | XWP500A | Quaternary amine | 159 mg/g | ND | ND | 33 mg/g |

ND—Not Determined

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention not merely those representative designs that were chosen to serve as exemplary illustrations. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. A method of making a guanidine-functionalized particle, comprising:
    reacting O-methylisourea hemisulfate with a linker molecule comprising the formula $(RO)_n R^a{}_{3-n} Si-S_m-X$ where RO is an alkoxy group comprising one or two carbons, or is an acetoxy group,
    where n is 1, 2 or 3,
    where $R^a$ is an unreactive group,
    where S is a spacer group comprising a backbone with m atoms,
    m is from 2-16, inclusive, and
    where X is a primary amine that is capable of reacting with the O-methylisourea to form a guanidine group;
    and,
    reacting at least one of the RO groups of the linker molecule with a hydroxyl group of the particle to form a covalent bond between the linker molecule and the particle.

2. The method of claim 1 wherein the $(RO)_n Si$ moiety comprises a trimethoxysilane moiety.

3. The method of claim 1 wherein the linker molecule is 3-aminopropyltrimethoxysilane.

4. The method of claim 1 wherein the $(RO)_n Si$ moiety comprises a triethoxysilane moiety.

5. The method of claim 1 wherein all m atoms of the backbone of the spacer group S are carbon atoms.

6. The method of claim 1 wherein m=3.

7. The method of claim 1 wherein the spacer group S comprises at least one hetero atom.

8. The method of claim 7 wherein the spacer group S comprises at least one secondary amine.

9. The method of claim 8 wherein the linker molecule is N-(2-aminoethyl)-3-aminopropyltrimethoxysilane.

10. The method of claim 1 wherein the step of reacting at least one of the RO groups of the linker molecule with a hydroxyl group of the particle to form a covalent bond between the linker molecule and the particle, is performed after the reacting of the O-methylisourea hemisulfate with the linker molecule.

11. The method of claim 1 wherein the step of reacting at least one of the RO groups of the linker molecule with a hydroxyl group of the particle to form a covalent bond between the linker molecule and the particle, is performed before the reacting of the O-methylisourea hemisulfate with the linker molecule.

12. The method of claim 1 wherein the particle is an insoluble inorganic porous particle.

13. The method of claim 12 wherein the particle comprises vitrous $SiO_2$.

14. The method of claim 13 wherein the particle comprises surface hydroxyl groups.

15. The method of claim 14 wherein the particle is a silica particle.

16. The method of claim 15 wherein the particle is a silica gel particle.

17. The method of claim 16 wherein the silica gel particle comprises a particle size of about 25-100 microns and a pore size of about 60-2000 Angstroms.

18. The method of claim 1 wherein residual hydroxyl groups are present on a surface of the particle after the reacting of the at least one of the RO groups of the linker molecule with a hydroxyl group of the particle to form a covalent bond between the linker molecule and the particle.

19. The method of claim 1 wherein the method does not include a step of equilibrating the particle in an atmosphere having a defined relative humidity prior to the reacting of the at least one of the RO groups of the linker molecule with a hydroxyl group of the particle to form a covalent bond between the linker molecule and the particle.

* * * * *

UNITED STATES PATENT AND TRADEMARK OFFICE
CERTIFICATE OF CORRECTION

PATENT NO. : 10,246,472 B2
APPLICATION NO. : 15/488716
DATED : April 2, 2019
INVENTOR(S) : George Griesgraber et al.

Page 1 of 1

It is certified that error appears in the above-identified patent and that said Letters Patent is hereby corrected as shown below:

In the Specification

Column 5
Line 23, Delete "N-3 [" and insert -- N-3[ --, therefor.

Column 15
Line 1, Delete "DIASOGEL" and insert -- DAISOGEL --, therefor.

Column 15
Line 15 (Approx.), Delete "DIASOGEL" and insert -- DAISOGEL --, therefor.

Column 16
Line 2, Delete "DIASOGEL" and insert -- DAISOGEL --, therefor.

Column 16
Line 58, Delete "DIASOGEL" and insert -- DAISOGEL --, therefor.

Column 17
Lines 1-2, Delete "DIASOGEL" and insert -- DAISOGEL --, therefor.

Column 17
Line 25, Delete "DIASOGEL" and insert -- DAISOGEL --, therefor.

In the Claims

Column 19
Line 7, In Claim 13, delete "vitrous" and insert -- vitreous --, therefor.

Signed and Sealed this
Twenty-fourth Day of December, 2019

Andrei Iancu
*Director of the United States Patent and Trademark Office*